US012514729B1

(12) United States Patent
Theriot et al.

(10) Patent No.: US 12,514,729 B1
(45) Date of Patent: Jan. 6, 2026

(54) WALKING BOOT APPARATUS

(71) Applicant: ManaMed, LLC, Denton, TX (US)

(72) Inventors: Trevor Theriot, Denton, TX (US); Kelly Nolan, Denton, TX (US)

(73) Assignee: ManaMed, LLC, Denton, TX (US)

( * ) Notice: Subject to any disclaimer, the term of this patent is extended or adjusted under 35 U.S.C. 154(b) by 72 days.

(21) Appl. No.: 18/426,643

(22) Filed: Jan. 30, 2024

(51) Int. Cl.
*A61F 5/01* (2006.01)
*A43B 7/20* (2006.01)

(52) U.S. Cl.
CPC ............... *A61F 5/0111* (2013.01); *A43B 7/20* (2013.01); *A61F 5/0127* (2013.01)

(58) Field of Classification Search
CPC .... A61F 5/0111; A61F 5/0195; A61F 5/0127; A43B 7/18; A43B 7/20
See application file for complete search history.

(56) References Cited

U.S. PATENT DOCUMENTS 7,618,388 B1 * 11/2009 Chan ..................... A61F 5/0195 128/882
9,039,645 B2 5/2015 Arnold et al.
10,449,077 B2 10/2019 Grim et al.
2002/0193717 A1 * 12/2002 Burns ..................... A61F 5/012 602/6
2007/0293798 A1 * 12/2007 Hu ........................ A61F 5/0195 602/27
2010/0100020 A1 * 4/2010 Fout ...................... A61F 5/0195 602/23
2012/0035520 A1 * 2/2012 Ingimundarson ..... A61F 5/0195 602/23
2013/0018294 A1 * 1/2013 Jones ........................ A61F 5/30 602/27
2014/0276301 A1 9/2014 Grim et al.
2016/0213506 A1 * 7/2016 Chen ......................... A61F 5/30
2018/0338852 A1 11/2018 Grim et al.

* cited by examiner

*Primary Examiner* — Keri J Nelson
(74) *Attorney, Agent, or Firm* — Holland & Knight LLP; Matthew C. Cox; Forrest S. Tinnin

(57) ABSTRACT

The present disclosure provides for a walking boot apparatus. The apparatus may include a base, uprights extending from the base and struts disposed in openings on the uprights. The apparatus may further include a bar disposed on one or both struts. A bar may be configured to be bent towards or away from the leg, such that the bar biases a strut towards or away from the leg. The apparatus may further include a sleeve disposed between the first upright and the second upright, which may include an inflatable bladder.

8 Claims, 16 Drawing Sheets

WALKING BOOT APPARATUS

CROSS-REFERENCES TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING OR COMPUTER PROGRAM LISTING INDEX

Not applicable.

BACKGROUND

The present invention relates generally to orthopedic devices, and more particularly to walking boot apparatuses.

Heel and ankle injuries are often treated by securing the position of the ankle in a desirable (e.g., neutral) position by securing the leg within a walking boot, which typically encases the leg in a hard plastic cast unit until the healing is complete. Conventional walking boots may include upright support members that prevent the leg from pivoting inwards or outwards relative to the ankle, and may secure the leg to such support structures using a sleeve that is wrapped about the leg and secured to such support structures. However, conventional walking boots are often rigid and do not allow the leg to be positioned at an ideal position that may slightly depart from the precise neutral position. Furthermore, conventional walking boots often allow the leg to move about more than intended due to limitations of the securing force of the sleeve, thereby delaying healing.

It would be advantageous to provide a walking boot that facilitates desirable adjustments of the leg relative to the ankle, as well as enhanced securing of the leg on the walking boot once said desirable position has been attained.

What is needed, therefore, are improved apparatuses for walking boots.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides for a walking boot apparatus. The apparatus may include a base configured to support a foot of a leg and secure an ankle of the leg. The apparatus may further include a first upright extending from the base. The first upright may include a first opening. The apparatus may further include a second upright extending from the base. The second upright may include a second opening. The apparatus may further include a first strut disposed in the first opening, as well as a second strut disposed in the second opening. The apparatus may further include a first bar disposed on the first strut. The first bar may be configured to be bent towards or away from the leg, such that the first bar biases the first strut towards or away from the leg. The apparatus may further include a second bar disposed on the second strut. The second bar may be configured to be bent towards or away from the leg, such that the second bar biases the second strut towards or away from the ankle. The apparatus may further include a sleeve disposed between the first upright and the second upright.

In some embodiments, the sleeve includes a bladder. The apparatus may further include a valve disposed on the bladder. The valve may be configured to inject air into the bladder. The apparatus may further include a push-button disposed on the valve. The valve may be biased to a closed position, while the push-button may be biased to an uncompressed position. When the push-button is compressed, the valve may open and air may be injected into the valve. When the push-button returns to the uncompressed position, the valve may close.

In some embodiments, the first strut includes a first biasing member configured to secure the first strut relative to the first upright when the first strut is inserted within the first opening, and the second strut includes a second biasing member configured to secure the second strut relative to the second upright when the second strut is inserted within the second opening.

In some embodiments, the first opening includes a first spine, and the first strut further includes a first slot corresponding to the first spine, such when the first strut is inserted within the first opening, the first spine is guided through the first slot to align the first strut relative to the first upright. The second opening may include a second spine, and the second strut may further include a second slot corresponding to the second spine, such when the second strut is inserted within the second opening, the second spine is guided through the second slot to align the second strut relative to the second upright.

In some embodiments, the first bar includes a first number of locating holes, the first strut includes a first number of alignment openings, and the first number of locating holes are aligned with the first number of alignment openings. The second bar may include a second number of locating holes, the second strut may further include a second number of alignment openings, and the second number of locating holes may be aligned with the second number of alignment openings.

Numerous other objects, advantages and features of the present disclosure will be readily apparent to those of skill in the art upon a review of the following drawings and description of a preferred embodiment.

DETAILED DESCRIPTION

Figure 1A:
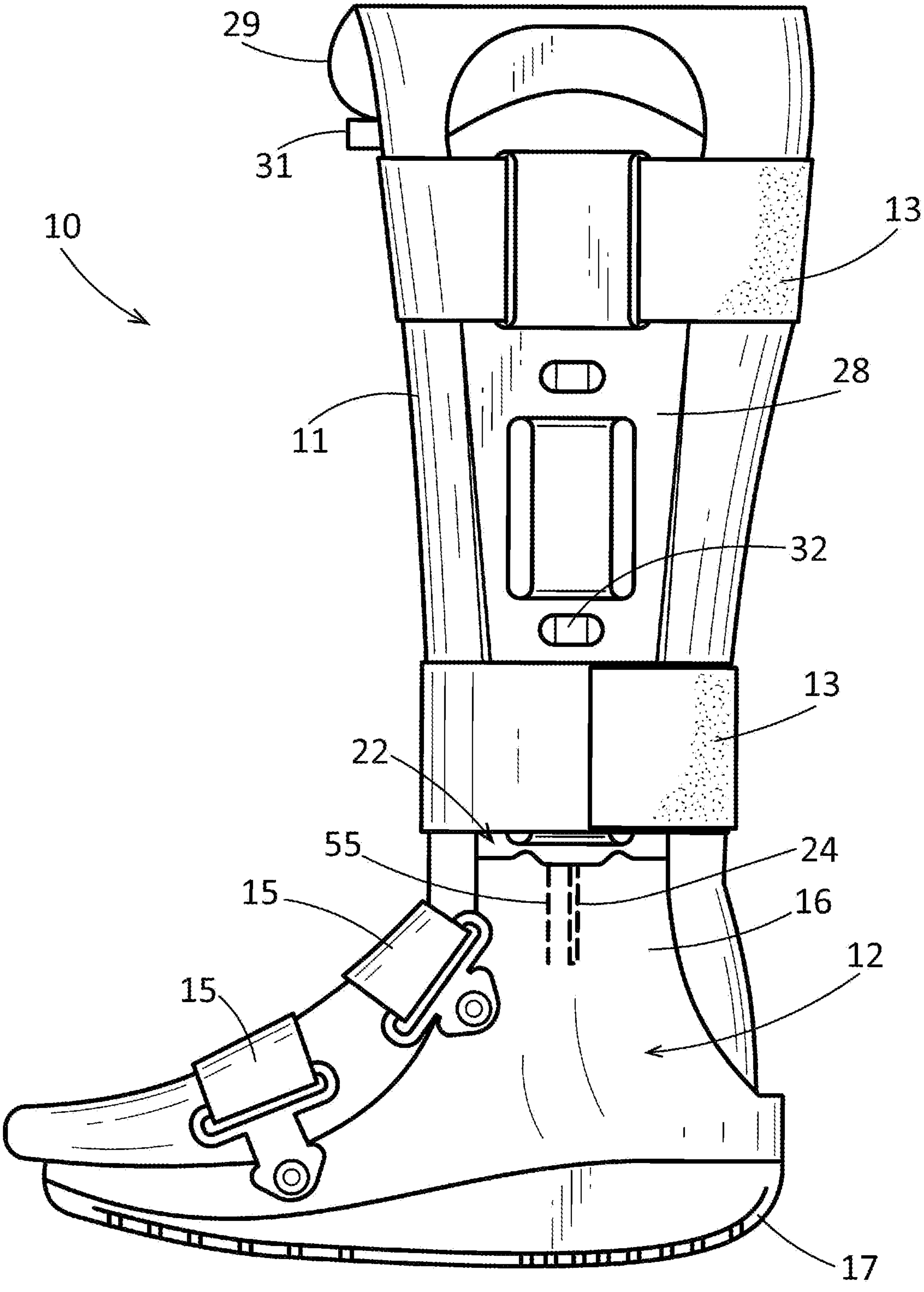
FIG. 1A is a right side view of a tall walking boot apparatus, according to some embodiments of the present disclosure.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatuses, systems, and methods described herein. Such equivalents are considered to be within the scope of this disclosure and may be covered by the claims.

Furthermore, the described features, structures, or characteristics of the disclosure may be combined in any suitable manner in one or more embodiments. In the description contained herein, numerous specific details are provided, such as examples of programming, software, user selections, hardware, hardware circuits, hardware chips, or the like, to provide understanding of embodiments of the disclosure. One skilled in the relevant art will recognize, however, that the disclosure may be practiced without one or more of the specific details, or with other methods, components, materials, apparatuses, devices, systems, and so forth. In other instances, well-known structures, materials, or operations may not be shown or described in detail to avoid obscuring aspects of the disclosure.

The aforementioned features and advantages of the embodiments will become more fully apparent from the description and appended claims, or may be learned by the practice of embodiments as set forth herein. As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present disclosure may take the form of a computer program product embodied in one or more computer-readable media having program code embodied thereon.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The words "connected", "attached", "joined", "mounted", "fastened", and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Figure 1B:
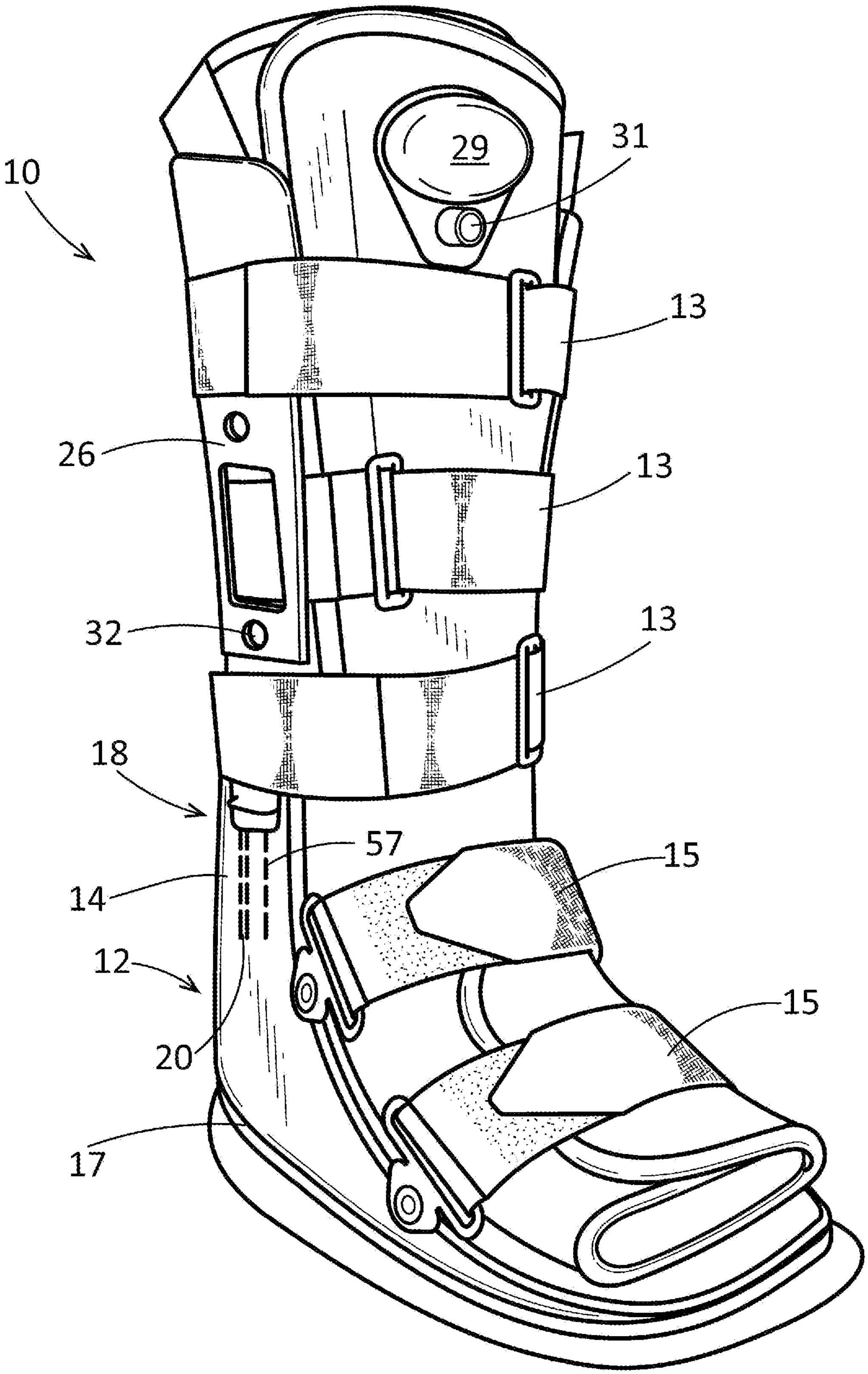
FIG. 1B is a left perspective view of a tall walking boot apparatus, according to some embodiments of the present disclosure.
Figure 1C:
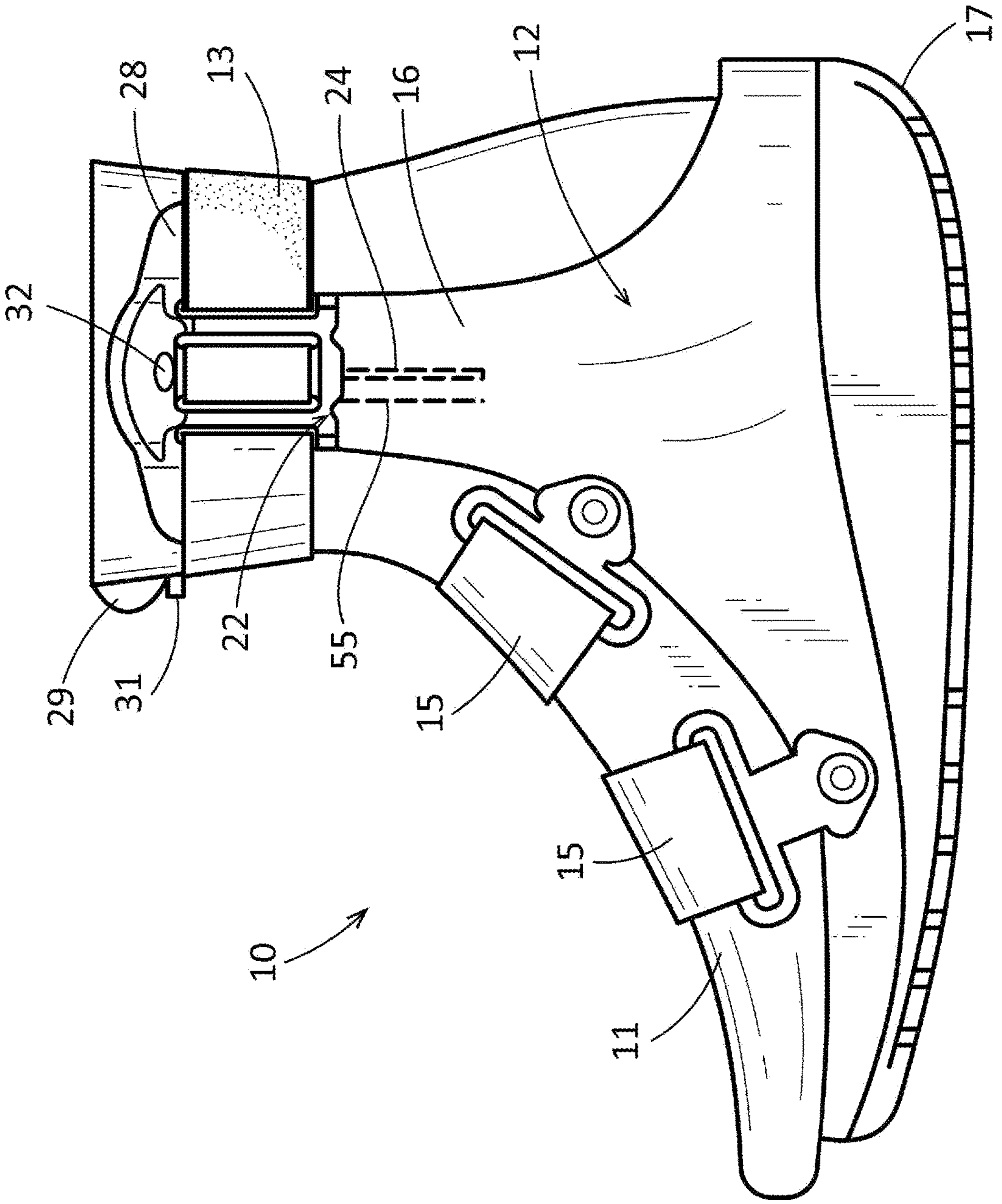
FIG. 1C is right side view of a short walking boot apparatus, according to some embodiments of the present disclosure.
Figure 1D:
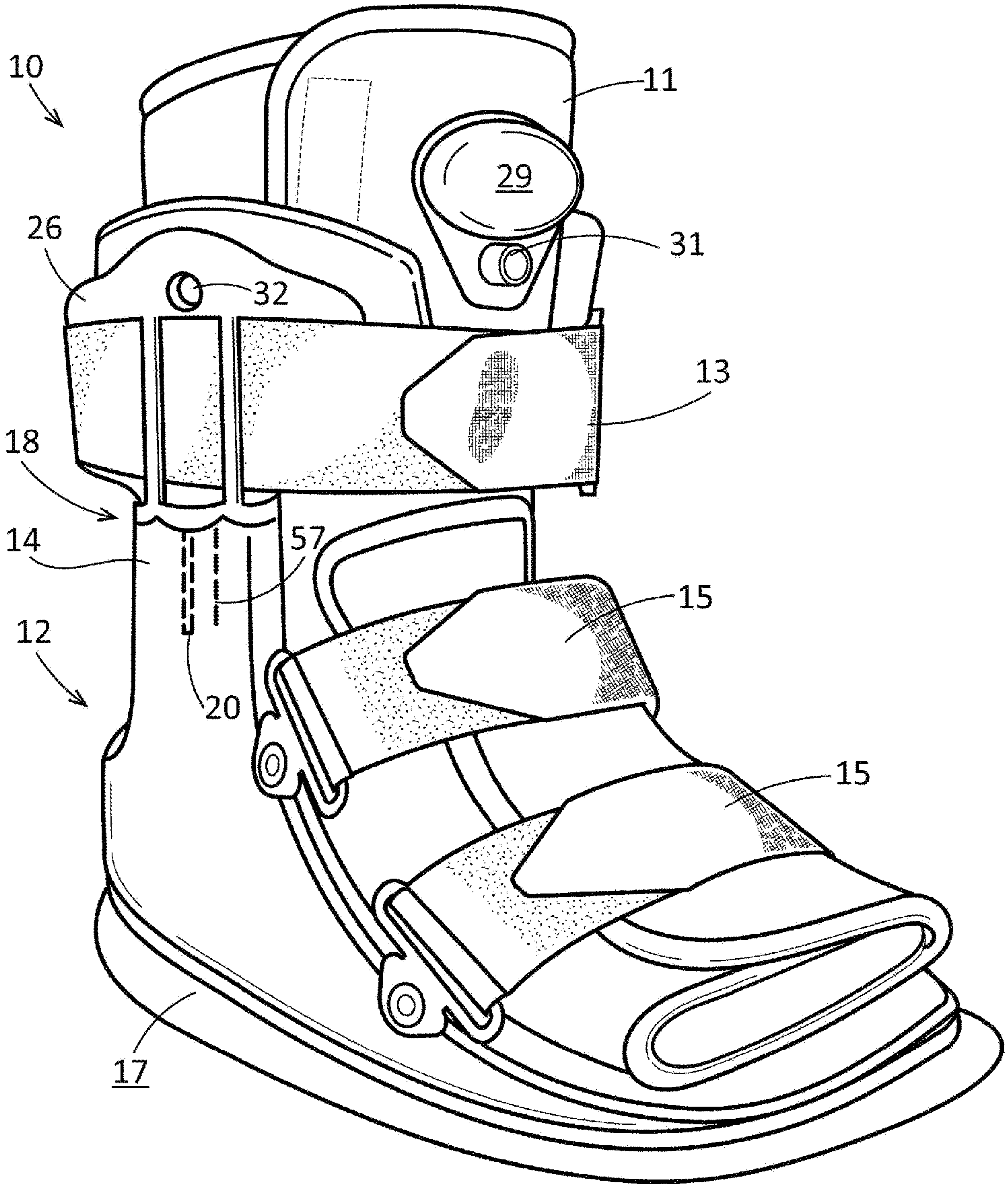
FIG. 1D is a left perspective view of a short walking boot apparatus, according to some embodiments of the present disclosure.

Referring now to FIGS. 1A-1D, a walking boot apparatus (apparatus) 10 is shown, according to various embodiments of the present disclosure. In some embodiments, the apparatus 10 is configured as a tall walking boot that provides enhanced support to the ankle. In other embodiments, the apparatus 10 is configured as a short walking boot that provides enhanced mobility to the user, while still providing adequate support. FIG. 1A thus depicts a right side of a tall configuration of the apparatus 10; FIG. 1B depicts a left side of the tall configuration of the apparatus 10; FIG. 1C depicts a left side of a short configuration of the apparatus 10; and FIG. 1D depicts a right side of the short configuration of the apparatus 10, according to some embodiments.

The apparatus 10 may include a base 12, which may be configured to support a foot of a leg and secure an ankle of the leg. The apparatus 10 may further include a pair of uprights disposed on and extending upwards from the base 12. Such uprights may be configured to surround and secure an ankle of the user. For instance, the apparatus 10 may include a first (e.g., left) upright 14 extending from the base 12 and a second (e.g., right) upright 16 extending from the base 12. In some embodiments, the apparatus 10 further includes a sleeve 11 disposed between the first upright 14 and the second upright 16. For instance, the sleeve 11 may be wrapped around the leg in order to secure the leg on the apparatus 10. As discussed in greater detail below, the sleeve 11 may be configured to provide compression to the leg.

The apparatus 10 may further include support structures for securing the position of the leg relative to the ankle. Such support structures may be bilateral struts that form a bilateral orthopedic walking boot when assembled with the base 12. For instance, the apparatus 10 may include a first (e.g., left) strut 26 and a second (e.g., right) strut 28.

The first and second struts 26, 28 may be secured to a leg of the user with upper straps 13 that encircle at least a portion of the leg, and may be relatively rigid in response to user motion (e.g., the user walking with the apparatus 10 on their foot). For instance, walking boots are typically configured to encase the leg such that the foot and ankle are immobilized at a neutral position (e.g., ninety degrees).

Additionally, the base 12 may be secured to the foot of the user with lower straps 15. The first and second struts 26, 28 may be rigid enough to maintain the position of the ankle in an ideal neutral position. However, as discussed in greater detail below with reference to FIG. 4, the first and second struts 26, 28 may be adjustable. For instance, depending on the nature of the ankle injury, a slightly different angular position of the ankle may be advantageous. The first and/or second struts 26, 28 may be configured to be bent (e.g., deflected) such that the apparatus 10 immobilizes the foot and ankle at a desired position, and retains such desired deflection during use.

Figure 2A:
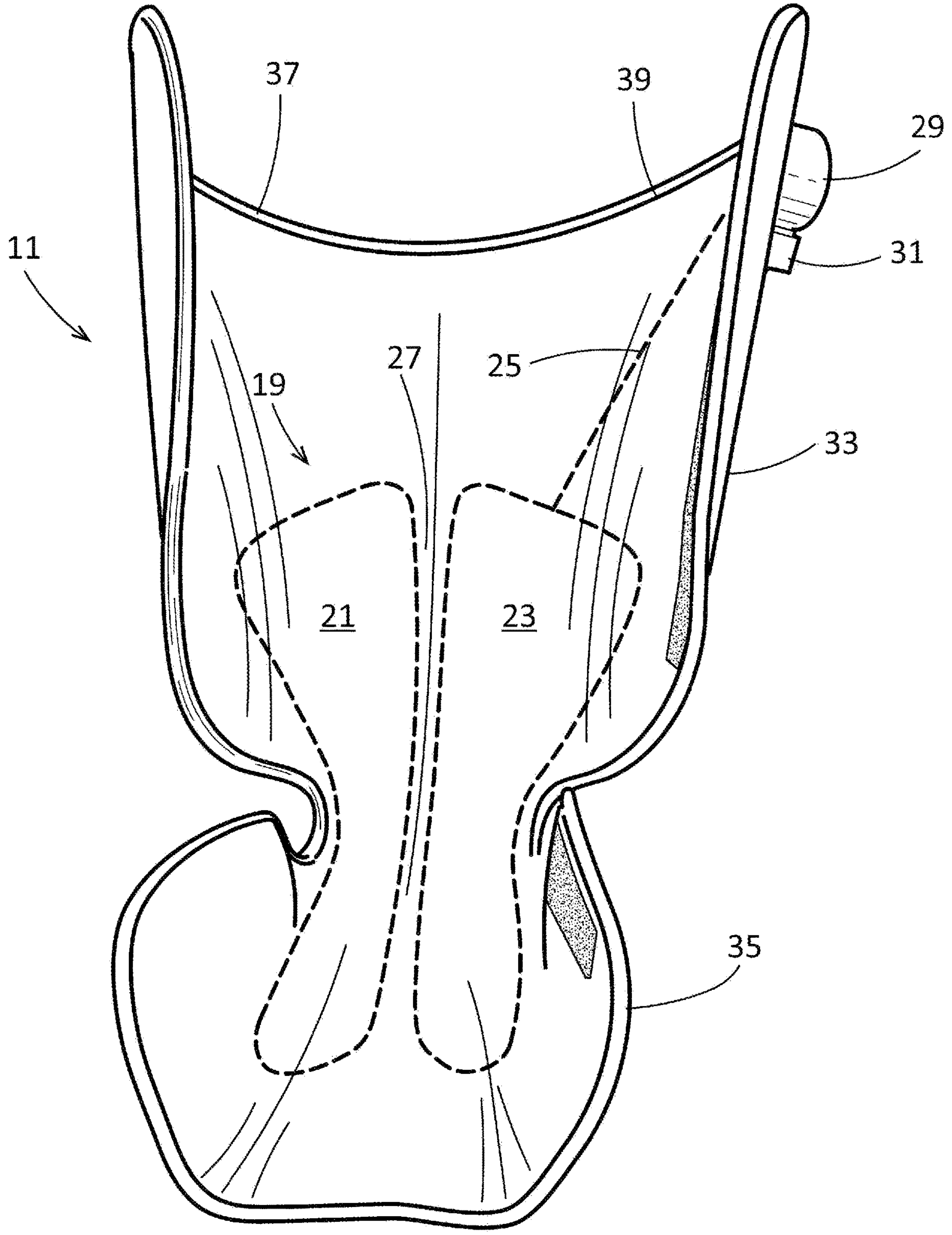
FIG. 2A is a perspective view of an opened sleeve for a tall walking boot apparatus, according to some embodiments of the present disclosure.
Figure 2B:
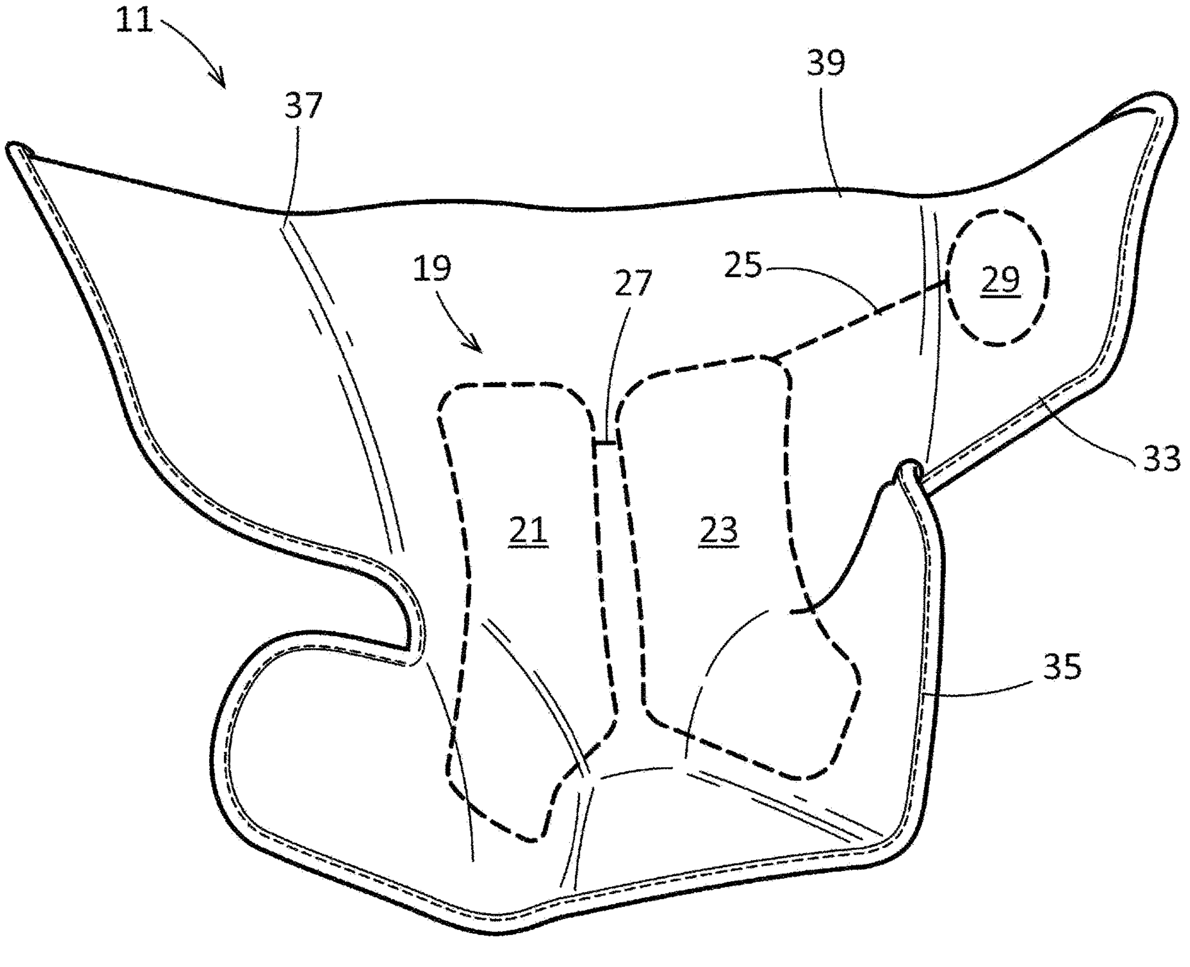
FIG. 2B is a perspective view of an opened sleeve for a short walking boot apparatus, according to some embodiments of the present disclosure.

Referring now to FIGS. 1A-2B, the sleeve 11 may include a bladder 19, according to some embodiments of the present disclosure. FIG. 2A depicts the sleeve 11 of the tall configuration of the apparatus 10, while FIG. 2B depicts the sleeve 11 of the short configuration of the apparatus 10, according to some embodiments.

The bladder 19 may be filled with air in order to secure the leg within the sleeve 11. In some embodiments, the apparatus 10 further includes a valve 31 disposed on the bladder 19 or the sleeve 11. For example, the valve 31 may be configured to inject air into the bladder 19 via a valve tube 25. In some embodiments, the valve 31 is operated via a pneumatic pump. For instance, the apparatus 10 may further include a push-button 29 disposed on the valve 31. The push-button 29 may be configured to open and close the valve 31, thus allowing air to travel into the bladder 19 via the valve tube 25.

In some embodiments, the valve 31 is biased to a closed position and the push-button 29 is biased to an un-compressed position (as shown). When the push-button 29 is compressed, the valve 31 may open and air may be injected into (e.g., pulled through) the valve 31. Conversely, when the push-button 29 is uncompressed, the valve 31 may close. In this sense, compressing the push-button 29 may pack together air molecules therein and increase there pressure; when the air pressure is high enough, the valve 31 (operating as a one-way valve) allows the pressurized air to flow through the valve tube 25 into the bladder 19.

In some embodiments, the bladder 19 is arranged in two chambers. For instance, the bladder 19 may include a first (e.g., left) chamber 21 disposed on a first (e.g., left) side 37 of the sleeve 11, as well as a second (e.g., right) chamber 23 disposed on a second (e.g., right) side 39 of the sleeve 11. As air is injected into the bladder 19 via the valve tube 25, air may travel through the second chamber 23 and into the first chamber 21 via a chamber tube 27 that extends between the first and second sides 37, 39 of the sleeve 11. In some embodiments, the bladder 11 is arranged to extend between an upper portion 33 of the sleeve 11 and a lower portion 35 of the sleeve 11. For instance, the bladder 11 may extend down the upper portion 33 of the sleeve, navigate the curvature of the sleeve 11 about the heel of the user, and extend towards the foot of the user on the lower portion 35 of the sleeve. Accordingly, the bladder 19 may be configured to provide compression to a left-upper side of the ankle; a left-lower side of the ankle; a right-upper side of the ankle; and a right-lower side of the ankle. It should be appreciated that the bladder 19 may be configured in any number of manners, incorporating some or all of the various portions depicted herein in order to provide a desired compression to the ankle.

Referring again to FIGS. 1A-1D, and as mentioned above, the base 12 may include the first and second uprights 14, 16. The first upright 14 may include a first opening 18, while the second upright 16 may include a second opening 22. The first strut 26 may be disposed in the first opening 18, while the second strut 28 may be disposed in the second opening 22.

In some embodiments, the first upright 14 includes a first spine 20. Additionally, the first opening 18 may include a first key 57. As discussed in greater detail below with reference to FIGS. 3A-3H, the first strut 26 may include a first slot 34 corresponding to the first spine 20, such that when the first strut 26 is inserted within the first opening 18, the first spine 20 is guided through the first slot 34 to align the first strut 26 relative to the first upright 14. Further, the first strut 26 may include a first guide 38 corresponding to the first key 57, such that the first key 57 is similarly guided through the first guide 38. In this sense, the first spine 20 may extend parallel to the first key 57, which may be laterally offset from the first spine 20. Of course, the second opening 22 may include a second spine 24 and a second key 67, which may operate in similar correspondence with a second slot 44 and a second guide 48 on the second strut 28. Thus, the first and second spines 20, 24, as well as the first and second keys 57, 67, may be configured to facilitate alignment of the first and second struts 26, 28 relative to the first and second uprights 14, 16 when the first and second struts 26, 28 are disposed in the first and second openings 18, 22.

Figure 3A:
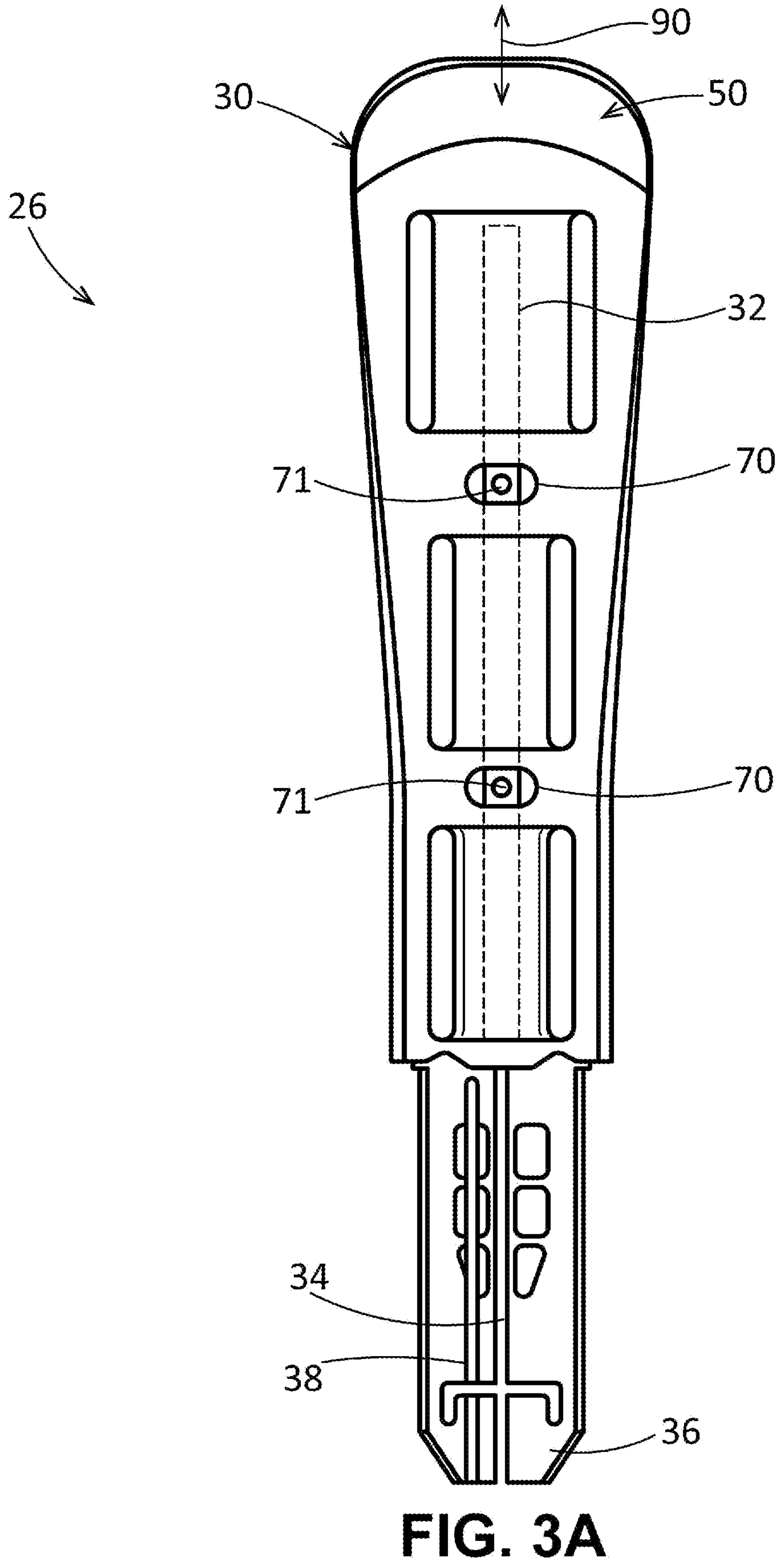
FIG. 3A is an outer side view of a left strut for a tall walking boot apparatus, according to some embodiments of the present disclosure.
Figure 3B:
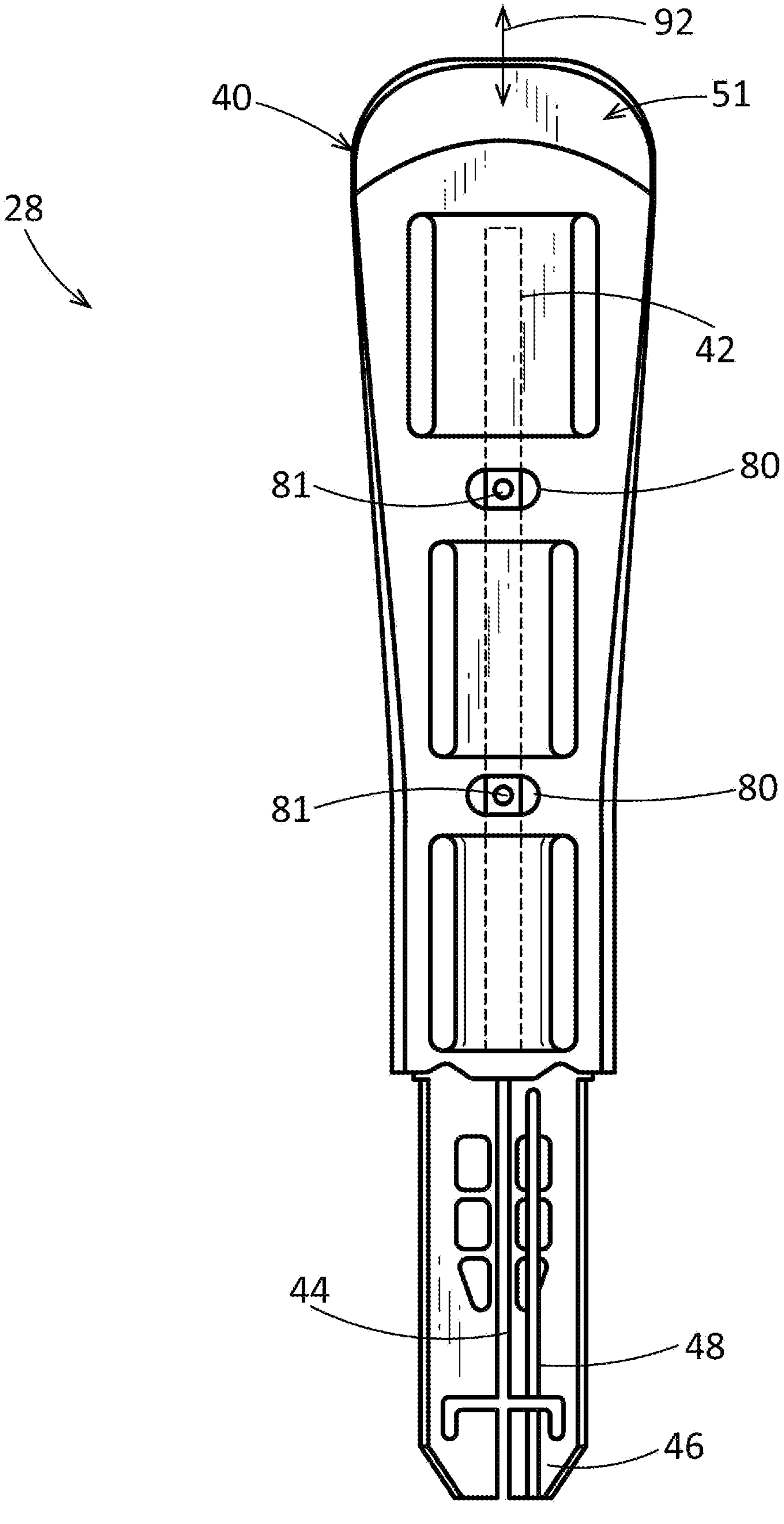
FIG. 3B is an outer side view of a right strut for a tall walking boot apparatus, according to some embodiments of the present disclosure.
Figure 3C:
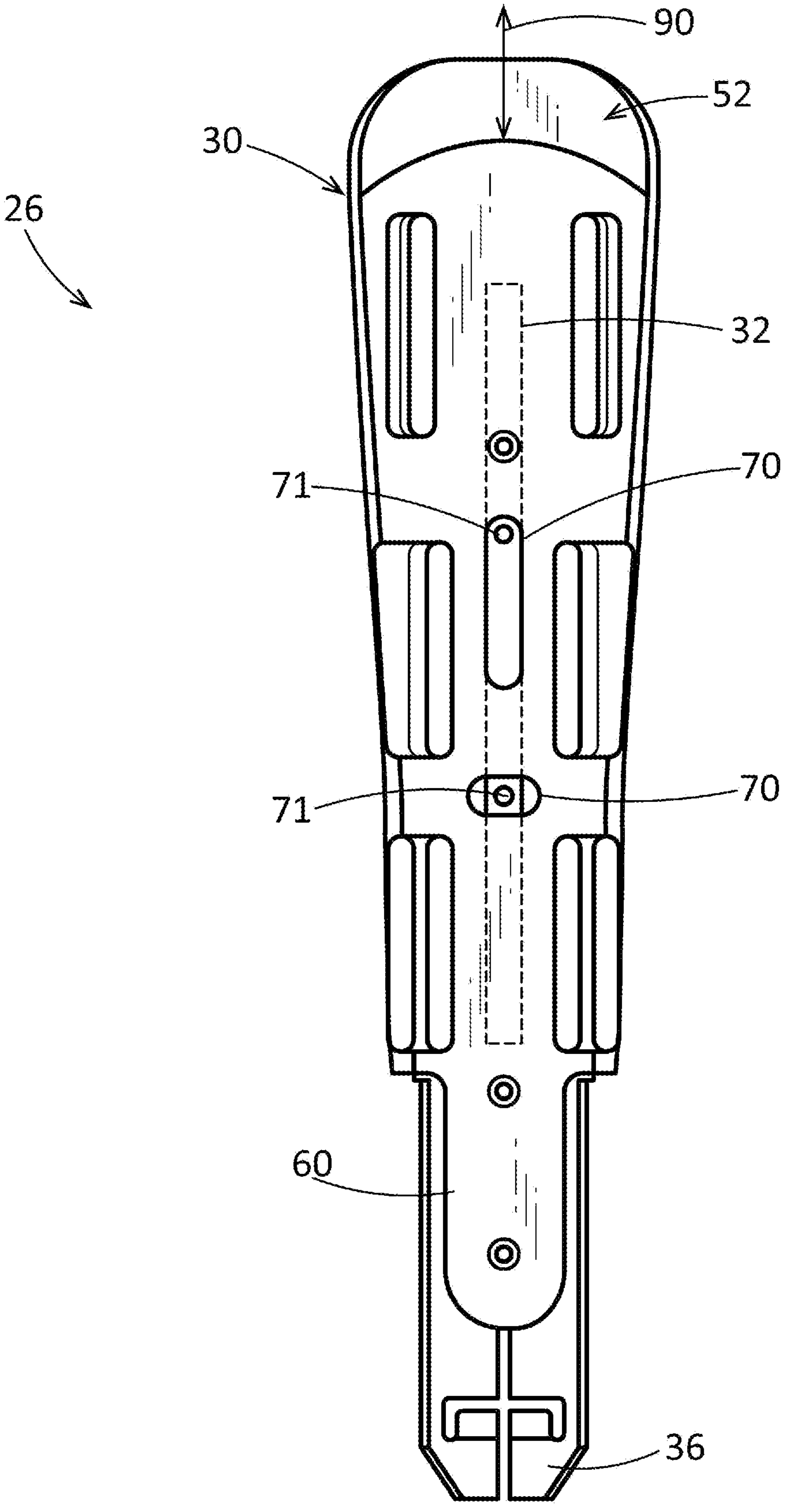
FIG. 3C is an inner side view of a left strut for a tall walking boot apparatus, according to some embodiments of the present disclosure.
Figure 3D:
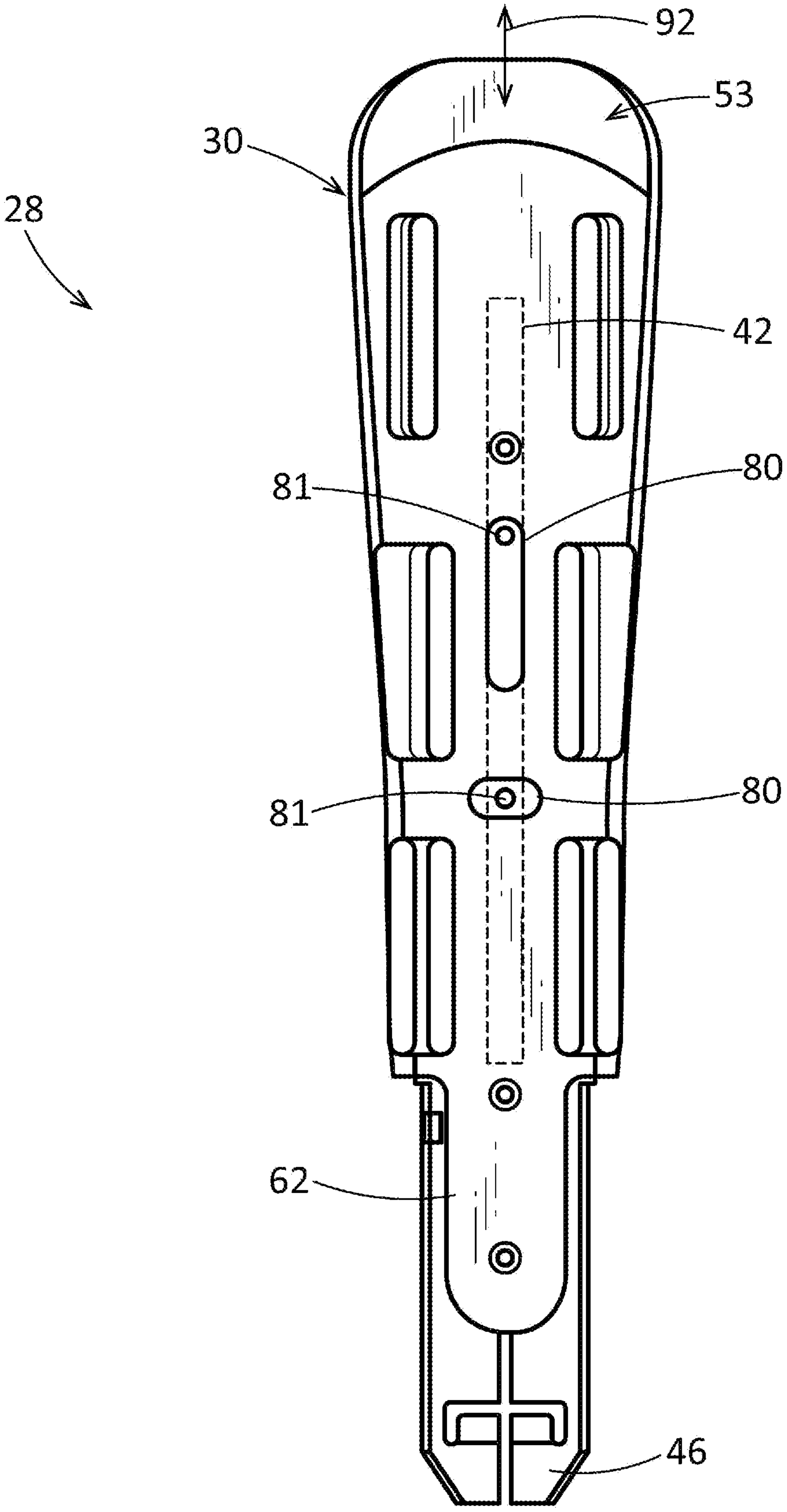
FIG. 3D is an inner side view of a right strut for a tall walking boot apparatus, according to some embodiments of the present disclosure.
Figure 3E:
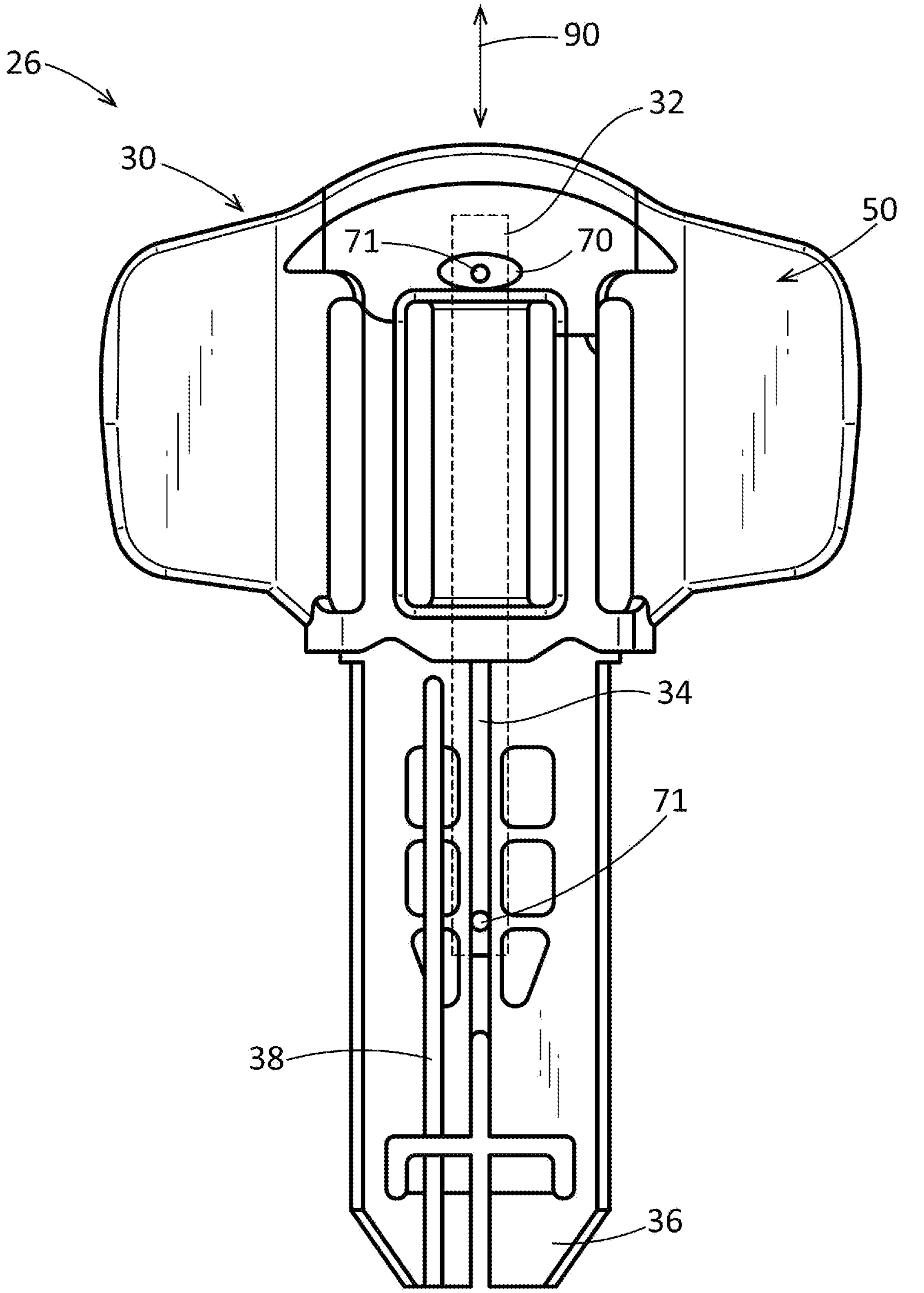
FIG. 3E is an outer side view of a left strut for a short walking boot apparatus, according to some embodiments of the present disclosure.
Figure 3F:
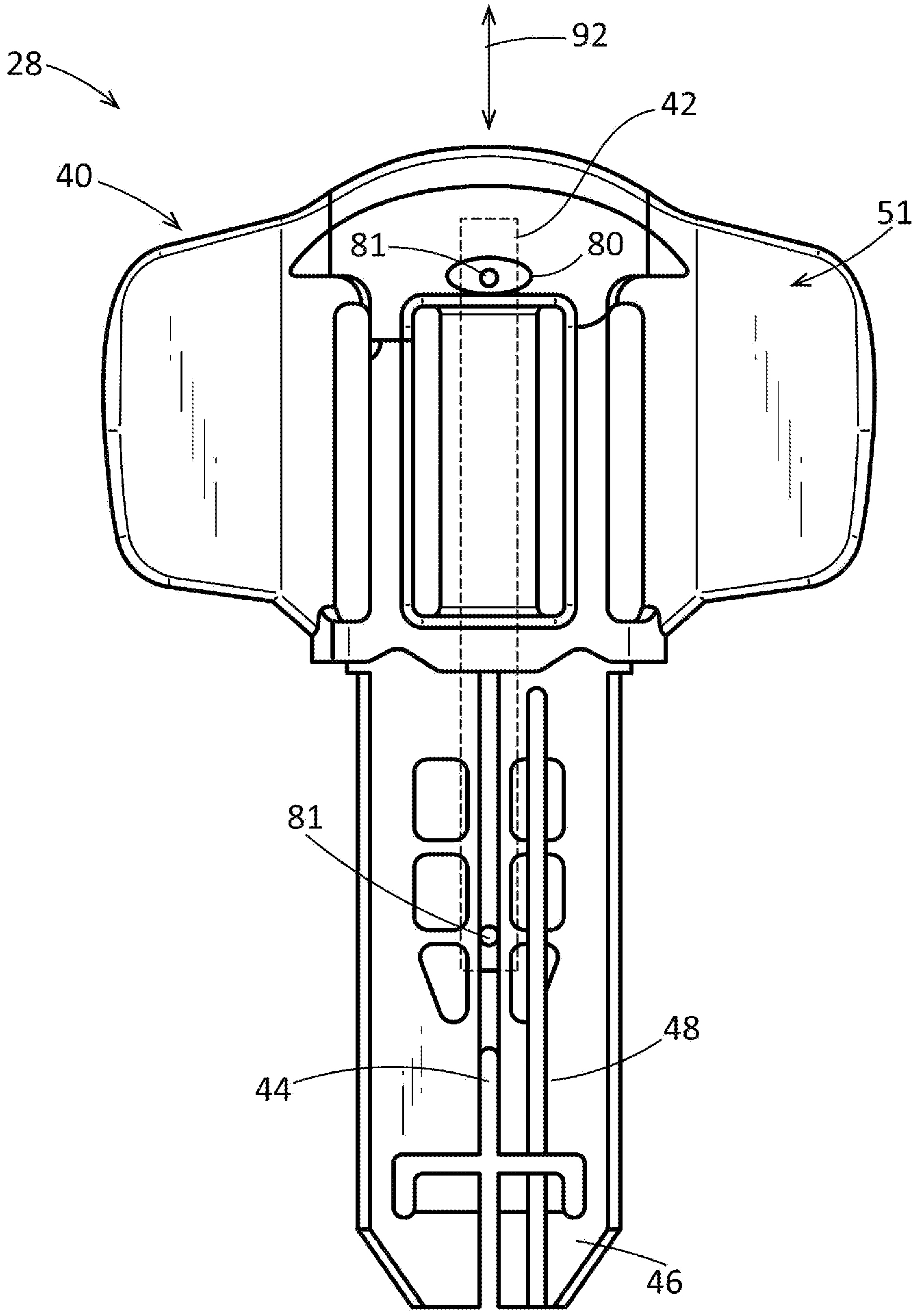
FIG. 3F is an outer side view of a right strut for a short walking boot apparatus, according to some embodiments of the present disclosure.
Figure 3G:
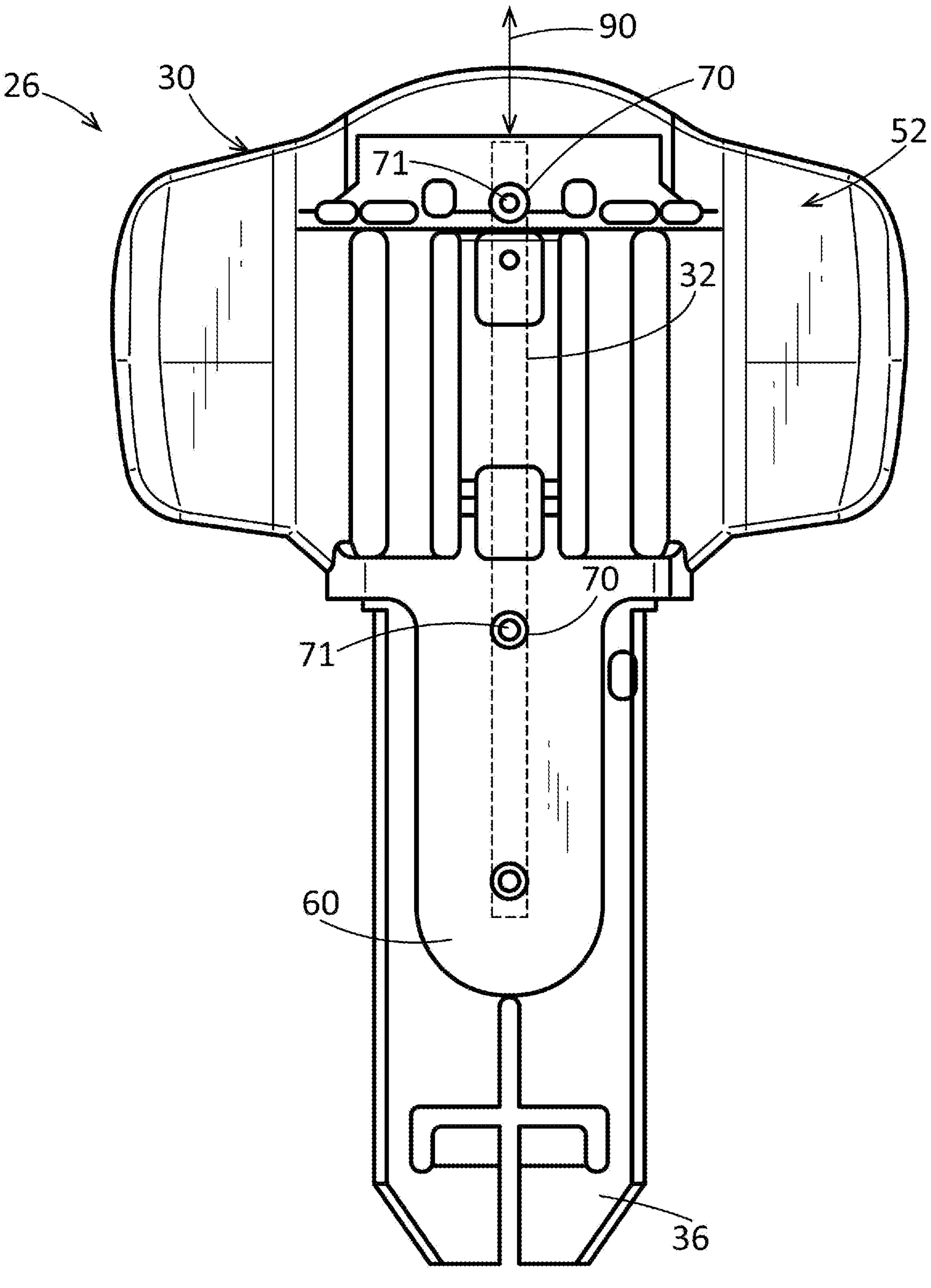
FIG. 3G is an inner side view of a left strut for a short walking boot apparatus, according to some embodiments of the present disclosure.
Figure 3H:
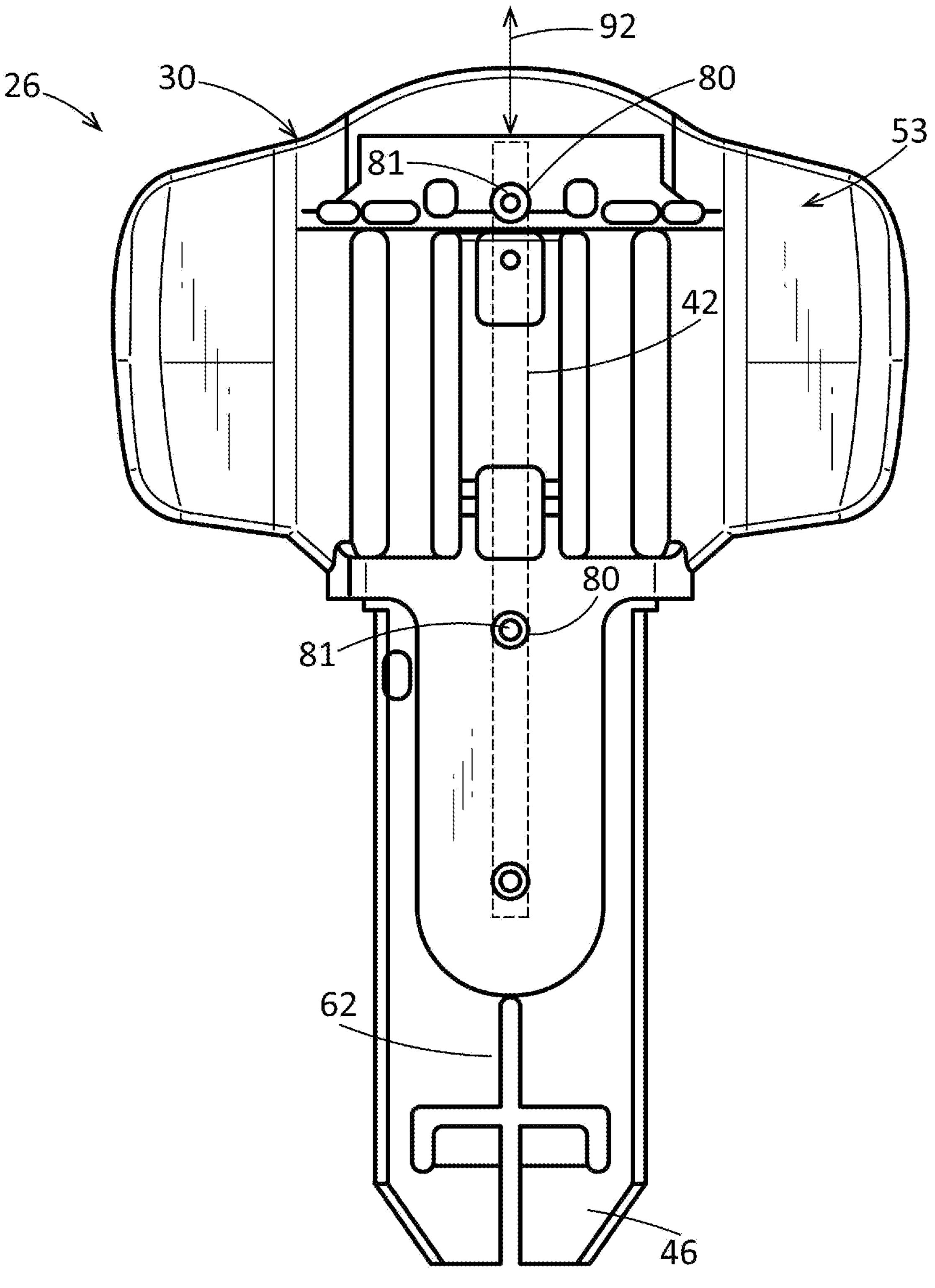
FIG. 3H is an inner side view of a right strut for a short walking boot apparatus, according to some embodiments of the present disclosure.
Figure 4:
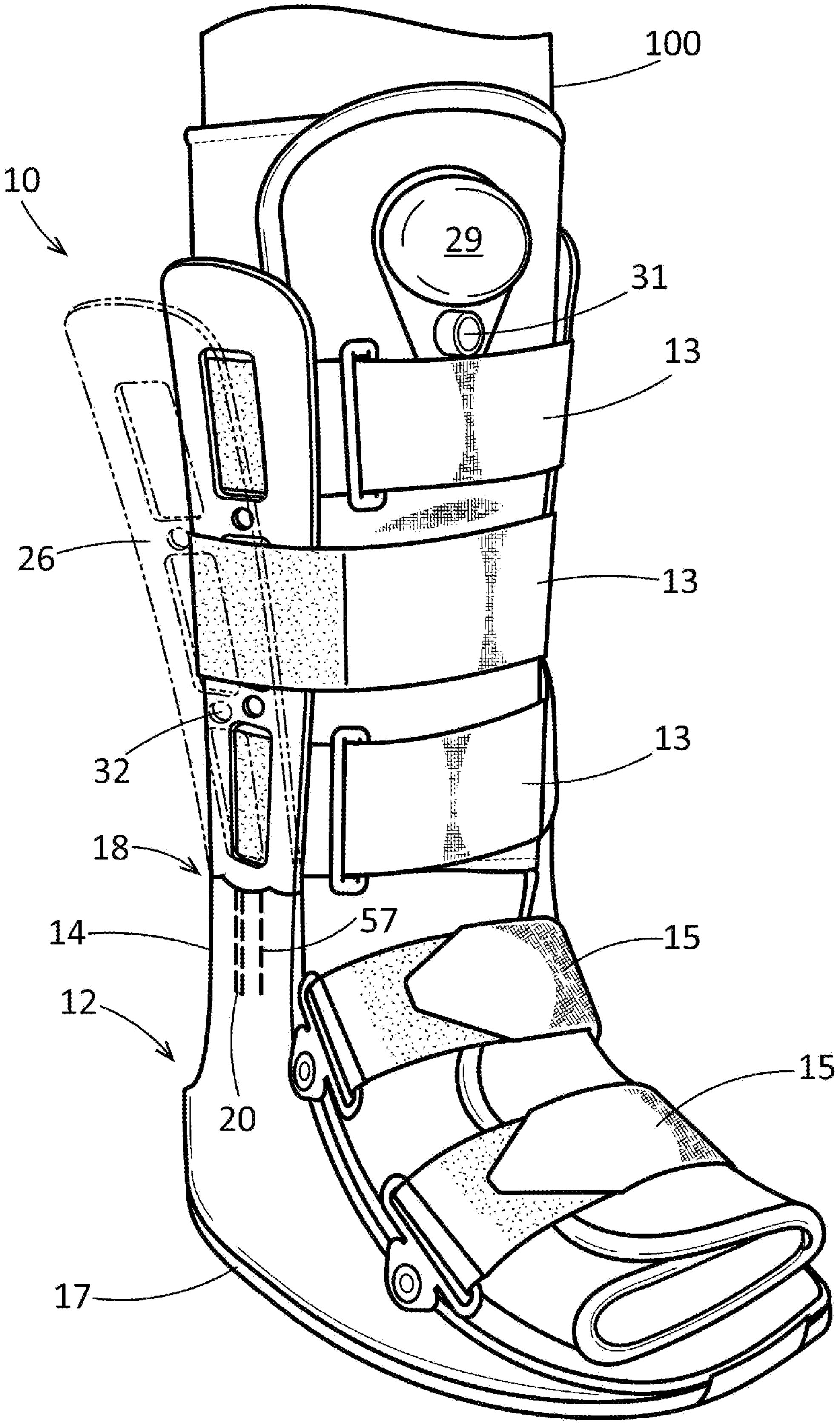
FIG. 4 is a left perspective view of a tall walking boot apparatus with a strut being adjusted, according to some embodiments of the present disclosure.

Referring now to FIGS. 3A-3H, and with additional reference to FIG. 4, the first and second struts 26, 28 are shown, according to various embodiments of the present disclosure. FIG. 3A depicts a first (e.g., outer) side 50 of the first strut 26 for a tall configuration of the apparatus 10; FIG. 3B depicts a first side 51 of the second strut 28 for a tall configuration of the apparatus 10; FIG. 3C depicts a second (e.g., inner) side 52 of the first strut 26 for a tall configuration of the apparatus 10; FIG. 3D depicts a second side 53 of the second strut 28 for a tall configuration of the apparatus 10; FIG. 3E depicts a first side 50 of the first strut 26 for a short configuration of the apparatus 10; FIG. 3F depicts a first side 51 of the second strut 28 for a short configuration of the apparatus 10; FIG. 3G depicts a second side 52 of the first strut 26 for a short configuration of the apparatus 10; and FIG. 3H depicts a second side 53 of the second strut 28 for a short configuration of the apparatus 10, according to some embodiments.

The first strut 26 may include a first elongate body 30. In some embodiments, the apparatus 10 further includes a first bar 32 (e.g., an elongate member, a shim, a rod, etc.) disposed on the first strut 26. Similarly, the second strut 28 may include a second elongate body 40 and a second bar 42 disposed thereon. The first and second elongate bodies 30, 40 may be semi-rigid and be made of any suitable material, including but not limited to plastic or rubber. The first and second bars 32, 42 may be semi-rigid and be made of any suitable material, including aluminum, plastic, or a composite. The first and second bars 32, 42 may be secured to (e.g., embedded with, molded within, fastened to, etc.) the first and second struts 26, 28, such that when the first and second bars 32, 42 are bent the first and second struts 26, 28 are bent, and vice-versa. However, the first and second bars 32, 42 may have different material properties than the first and second elongate bodies 30, 40. For instance, once bent or deflected (e.g., toward or away from a leg 100), as shown with reference to FIG. 4, the first and/or second bars 32, 42 may retain their bent shape and resist a bias of the first and/or second struts 26, 28 to return to their initial (e.g., fully upright) shape. In this sense, the first and second bars 32, 42 may be made of a shape-memory material that is malleable, while being less malleable than the material of the first and second struts 26, 28. Thus, the first and second bars 32, 42 may be configured to be bent towards or away from the ankle, such that the first and second bars 32, 42 biases the first and second struts 26, 28 (respectively) towards or away from the ankle. It should be appreciated that, although generally discussed herein as including each of the first bar 32 and the second bar 42, in further embodiments, the apparatus 10 only includes the first bar 32 or the second bar 42.

During assembly, the first and second bars 32, 42 may include one or more features that correspond to one or more features on the first and second elongate bodies 30, 40, in order to indicate a proper positioning of the first and second bards 32, 42 relative to the material of the first and second elongate bodies 30, 40. For instance, the first and second bars 32, 42 may include a number of locating holes 71, 81 (respectively). In turn, the first and second elongate bodies 30, 40 may include a number of alignment openings 70, 80 (respectively). As shown, when the first and second bars 32, 42 are properly positioned relative to the first and second elongate bodies 30, 40, the locating hole 71, 81 may be aligned with (e.g., visually positioned within) the first and second alignment openings 70, 80.

As mentioned above, the first and second elongate bodies 30, 40 may include first and second slots 34, 44 (respectively). The first slot 34 may be generally aligned with a first central longitudinal axis 90 of the first strut 26. Similarly, the second slot 44 may be generally aligned with a second central longitudinal axes 92. Additionally, the first and second elongate bodies 30, 40 may include first and second guides 38, 48. The first and second guides 38, 48 may be offset from the first and second central longitudinal axes 90, 92 (respectively).

As suggested above, the first and second openings 18, 22 may be configured to receive, align, and secure the first and second struts 26, 28 within the first and second uprights 14, 16. For instance, the first and second slots 34, 44 may correspond to the first and second spines 20, 24, of the first and second openings 18, 22, such that when the first and second struts 26, 28 are inserted within the first and second openings 18, 22, the first and second spines 20, 24 are guided through the first and second slots 34, 44 in order to align the first and second struts 26, 28 with the first and second uprights 14, 16. Thus, the first and second spines 20, 24 may be configured such that they are generally aligned with the first and second central longitudinal axes 90, 92 of the first and second elongate bodies 30, 40, thereby corresponding to the positions of the first and second slots 34, 44.

In order to ensure that the first and second struts 26, 28 are oriented properly when inserted within the first and second openings 18, 22, the first and second keys 55, 57 may be configured to correspond with the offset position of the first and second guides 38, 48. Further the first and second struts 26, 28 may include first and second inserts 60, 62 (respectively) on the back sides 52, 53 of the first and second struts 26, 28. Because of the corresponding offset positions of the first and second keys 55, 57, along with the position of the first and second guides 60, 62 on a particular side of the first and second struts 26, 28, the first strut 26 may only be positioned within the first opening 18 in the proper orientation shown herein (e.g., the first side 50 facing outwards), and the second strut 28 may only be positioned within the second opening 22 in the proper orientation shown herein, thus ensuring that inadvertent errors in assembly do not take place by a user or manufacturer.

In some embodiments, at or about proximal ends of the first and second elongate bodies 30, 40 (e.g., the end nearest to the base 12 when the apparatus is fully assembled as shown with reference to FIGS. 1A-1D), the first and second elongate bodies 30, 40 may include first and second biasing members 36, 46 (respectively) configured to secure the first and second struts 26, 28 relative to the first and second uprights 14, 16 when the first and second struts 26, 28 are inserted within the first and second openings 18, 22. For example, the first and second biasing members 36, 46 may each form a ramp that deflects when it is passed over a corresponding structure within the first and second uprights 14, 16 when the first and second struts 26, 28 are inserted within the first and second uprights 14, 16. Once the first and second biasing members 36, 46 pass over the corresponding structure within the first and second uprights 14, 16, the first and second biasing members 36, 46 may return to their original shapes, thus preventing the first and second struts 26, 28 from being removed from the first and second uprights 14, 16.

Figure 5:
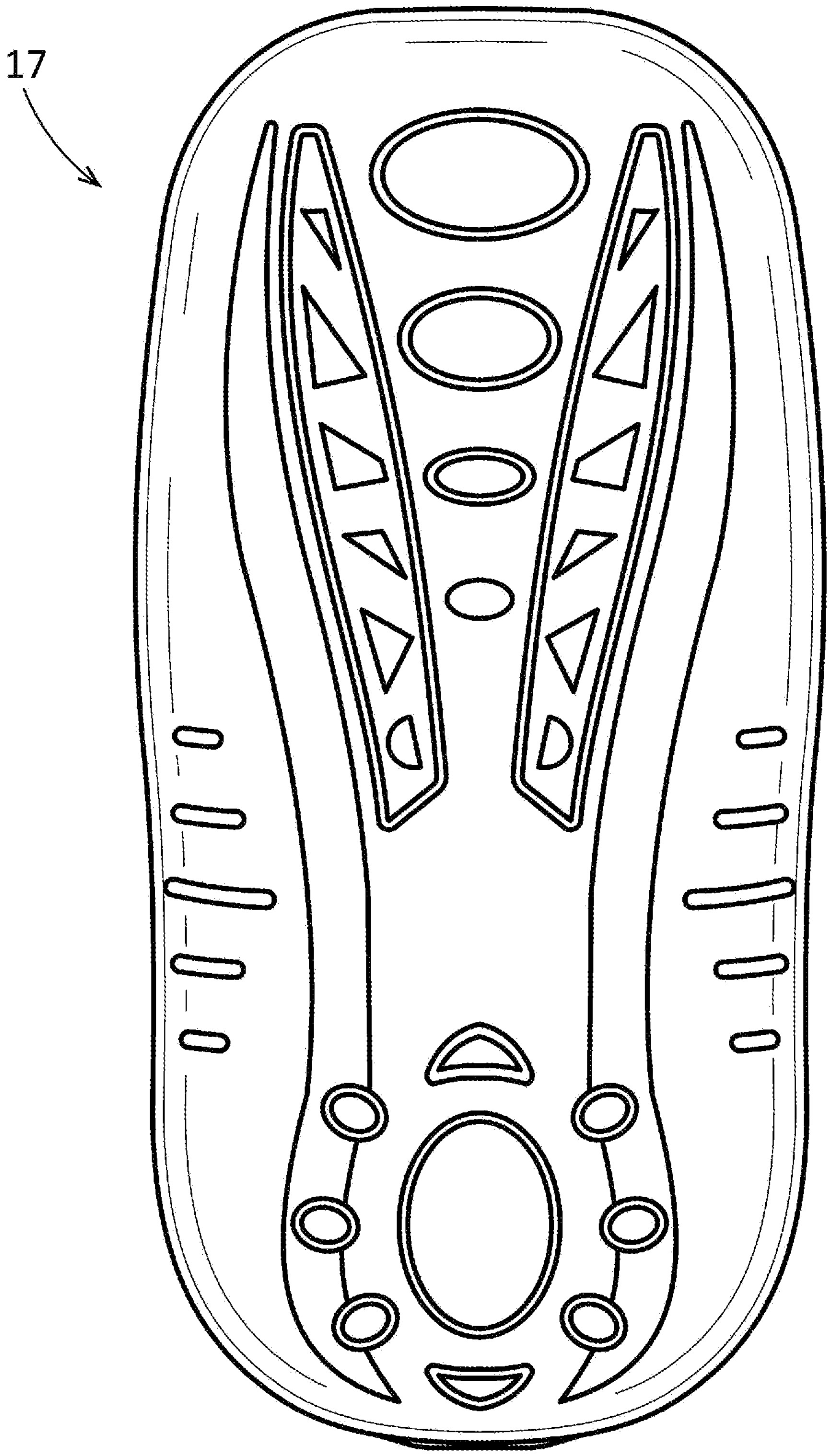
FIG. 5 is a lower view of a tread for a walking boot apparatus, according to some embodiments of the present disclosure.

Referring now to FIG. 5, a tread 17 of the apparatus 10 is shown, according to some embodiments of the present disclosure. The tread 17 may be secured to a bottom of the base 12. For instance, the tread 17 may be provided by over-molding a corresponding cavity on the bottom of the base 12. The tread 17 may be a non-planar bottom surface in order to facilitate enhanced mobility for a user walking in the apparatus 10.

Thus, although there have been described particular embodiments of the present invention of a new and useful KNEE WALKING BOOT APPARATUS it is not intended that such references be construed as limitations upon the scope of this invention.

What is claimed is:

1. A walking boot apparatus, comprising:
- a base configured to support a foot of a leg and secure an ankle of the leg;
- a first upright extending from the base, the first upright including a first opening;
- a second upright extending from the base, the second upright including a second opening;
- a first strut disposed in the first opening;
- a second strut disposed in the second opening;
- a first bar disposed on the first strut, the first bar configured to be bent towards or away from the leg, such that the first bar biases the first strut towards or away from the leg;
- a second bar disposed on the second strut, the second bar configured to be bent towards or away from the leg, such that the second bar biases the second strut towards or away from the leg; and
- a sleeve disposed between the first upright and the second upright, the sleeve including a bladder,
- wherein the first strut includes a first biasing member configured to secure the first strut relative to the first upright when the first strut is inserted within the first opening,
- wherein the second strut includes a second biasing member configured to secure the second strut relative to the second upright when the second strut is inserted within the second opening,
- wherein the first opening includes a first spine, and the first strut further includes a first slot corresponding to the first spine, such that when the first strut is inserted within the first opening, the first spine is guided through the first slot to align the first strut relative to the first upright,
- wherein the second opening includes a second spine, and the second strut further includes a second slot corresponding to the second spine, such that when the second strut is inserted within the second opening, the second spine is guided through the second slot to align the second strut relative to the second upright,
wherein the first bar includes a first plurality of locating holes,
wherein the first strut further includes a first plurality of alignment openings,
wherein the first plurality of locating holes are aligned with the first plurality of alignment openings,
wherein the second bar includes a second plurality of locating holes,
wherein the second strut further includes a second plurality of alignment openings, and
wherein the second plurality of locating holes are aligned with the second plurality of alignment openings.

2. The apparatus of claim 1, further comprising a valve disposed on the bladder, the valve configured to inject air into the bladder.

3. The apparatus of claim 2, further comprising a push-button disposed on the valve,
wherein the valve is biased to a closed position,
wherein the push-button is biased to an uncompressed position,
wherein when the push-button is compressed, the valve opens and air is injected into the valve, and
wherein when the push-button returns to the uncompressed position, the valve closes.

4. A walking boot apparatus, comprising:
a base configured to support a foot of a leg and secure an ankle of the leg;
a first upright extending from the base, the first upright including a first opening;
a second upright extending from the base, the second upright including a second opening;
a first strut disposed within the first opening;
a second strut disposed within the second opening;
a first bar disposed on the first strut, the first bar configured to be bent towards or away from the leg, such that the first bar biases the first strut towards or away from the leg; and
a second bar disposed on the second strut, the second bar configured to be bent towards or away from the leg, such that the second bar biases the second strut towards or away from the leg,
wherein the first strut includes a first biasing member configured to secure the first strut relative to the first upright when the first strut is inserted within the first opening,
wherein the second strut includes a second biasing member configured to secure the second strut relative to the second upright when the second strut is inserted within the second opening,
wherein the first opening includes a first spine, and the first strut further includes a first slot corresponding to the first spine, such that when the first strut is inserted within the first opening, the first spine is guided through the first slot to align the first strut relative to the first upright,
wherein the second opening includes a second spine, and the second strut further includes a second slot corresponding to the second spine, such that when the second strut is inserted within the second opening, the second spine is guided through the second slot to align the second strut relative to the second upright,
wherein the first bar includes a first plurality of locating holes,
wherein the first strut further includes a first plurality of alignment openings,
wherein the first plurality of locating holes are aligned with the first plurality of alignment openings,
wherein the second bar includes a second plurality of locating holes,
wherein the second strut further includes a second plurality of alignment openings, and
wherein the second plurality of locating holes are aligned with the second plurality of alignment openings.

5. The apparatus of claim 4, further comprising a sleeve disposed between the first upright and the second upright, the sleeve including a bladder.

6. The apparatus of claim 5, further comprising a valve disposed on the bladder, the valve configured to inject air into the bladder.

7. A walking boot apparatus, comprising:
a base configured to support a foot of a leg and secure an ankle of the leg;
a first upright extending from the base, the first upright including a first opening;
a second upright extending from the base, the second upright including a second opening;
a first strut disposed within the first opening and including a first biasing member configured to secure the first strut relative to the first upright when the first strut is inserted within the first opening;
a second strut disposed within the second opening and including a second biasing member configured to secure the second strut relative to the second upright when the second strut is inserted within the second opening;
a sleeve disposed between the first upright and the second upright, the sleeve including a bladder;
a valve disposed on the bladder and biased to a closed position;
a push-button disposed biased to an uncompressed position on the valve, the push-button configured to open and close the valve, wherein when the push-button is compressed the valve opens and air is injected into the valve, and when the push-button returns to the uncompressed position the valve closes; and
a first bar disposed on the first strut, the first bar configured to be bent towards or away from the leg, such that the first bar biases the first strut towards or away from the leg,
wherein the first opening includes a first spine, and the first strut further includes a first slot corresponding to the first spine, such that when the first strut is inserted within the first opening, the first spine is guided through the first slot to align the first strut relative to the first upright,
wherein the second opening includes a second spine, and the second strut further includes a second slot corresponding to the second spine, such that when the second strut is inserted within the second opening, the second spine is guided through the second slot to align the second strut relative to the second upright,
wherein the first bar includes a first plurality of locating holes and the first strut includes a first plurality of alignment openings,
wherein the first plurality of locating holes are aligned with the first plurality of alignment openings,
wherein the second bar includes a second plurality of locating holes and the second strut includes a second plurality of alignment openings, and wherein the second plurality of locating holes are aligned with the second plurality of alignment openings.

8. The apparatus of claim 7, further comprising a second bar disposed on the second strut, the second bar configured to be bent towards or away from the leg, such that the second bar biases the second strut towards or away from the leg.

* * * * *